US012765760B2

(12) United States Patent
Watanabe

(10) Patent No.: US 12,765,760 B2
(45) Date of Patent: Oct. 20, 2026

(54) ENDOSCOPE

(71) Applicant: HOYA CORPORATION, Tokyo (JP)

(72) Inventor: Toshiki Watanabe, Tokyo (JP)

(73) Assignee: PENTAX Medical Corporation, Tokyo (JP)

(*) Notice: Subject to any disclaimer, the term of this patent is extended or adjusted under 35 U.S.C. 154(b) by 260 days.

(21) Appl. No.: 18/284,979

(22) PCT Filed: Jun. 3, 2022

(86) PCT No.: PCT/JP2022/022610

§ 371 (c)(1),
(2) Date: Sep. 29, 2023

(87) PCT Pub. No.: WO2023/276551

PCT Pub. Date: Jan. 5, 2023

(65) Prior Publication Data

US 2024/0180412 A1 Jun. 6, 2024

(30) Foreign Application Priority Data

Jun. 30, 2021 (JP) ................................. 2021-109212

(51) Int. Cl.
*A61B 1/12* (2006.01)
*A61B 1/00* (2006.01)

(52) U.S. Cl.
CPC .......... *A61B 1/126* (2013.01); *A61B 1/00091* (2013.01)

(58) Field of Classification Search
CPC ............................ A61B 1/126; A61B 1/00091
See application file for complete search history.

(56) References Cited

U.S. PATENT DOCUMENTS 5,207,213 A * 5/1993 Auhll ..................... A61B 1/042 600/109
9,131,834 B2 * 9/2015 Kase .................... A61B 1/0676
11,042,020 B2 * 6/2021 Watanabe .......... A61B 1/00096
2008/0200764 A1 8/2008 Okada
2009/0253966 A1 * 10/2009 Ichimura ............ A61B 1/00181 600/158

(Continued)

FOREIGN PATENT DOCUMENTS

JP 2002-085339 A 3/2002
JP 2004-41426 A 2/2004

(Continued)

OTHER PUBLICATIONS

English Translation of—JP-2012245188-A on Espacenet (Year: 2012).*

(Continued)

*Primary Examiner* — Michael J Carey
*Assistant Examiner* — Megan Elizabeth Monahan
(74) *Attorney, Agent, or Firm* — Greenblum & Bernstein, P.L.C.

(57) ABSTRACT

An endoscope including a plurality of nozzles that injects a fluid toward an observation window, and an operation unit that operates the injection of the fluid by the nozzles, wherein a plurality of fluid channels that supplies the fluid from the operation unit to the nozzles is provided independently, and each nozzle performs the injection non-simultaneously.

11 Claims, 10 Drawing Sheets

(56) References Cited

U.S. PATENT DOCUMENTS

| | | | | |
|---|---|---|---|---|
| 2015/0005581 | A1* | 1/2015 | Salman | A61B 1/00181 600/156 |
| 2015/0018617 | A1* | 1/2015 | Aono | G02B 23/2415 600/157 |
| 2018/0084983 | A1* | 3/2018 | Okano | A61B 1/05 |
| 2019/0090723 | A1* | 3/2019 | Tanaka | A61B 1/00094 |
| 2019/0174999 | A1* | 6/2019 | Wake | A61B 1/00089 |
| 2019/0350449 | A1* | 11/2019 | Tajima | A61B 1/00 |
| 2020/0000320 | A1* | 1/2020 | Tajima | A61B 1/00163 |
| 2021/0177249 | A1 | 6/2021 | Watanabe | |
| 2022/0104696 | A1* | 4/2022 | Yan | A61B 1/00009 |
| 2022/0330802 | A1 | 10/2022 | Watanabe | |

FOREIGN PATENT DOCUMENTS

| | | | |
|---|---|---|---|
| JP | 2005-000567 | A | 1/2005 |
| JP | 2005-270216 | A | 10/2005 |
| JP | 2008-194375 | A | 8/2008 |
| JP | 2012245188 | A | * 12/2012 |
| JP | 2013-9896 | A | 1/2013 |
| JP | 3186191 | U | 8/2013 |
| JP | 2014132964 | A | * 7/2014 |
| JP | 2014-230673 | A | 12/2014 |
| JP | 2015-73689 | A | 4/2015 |
| JP | 2020-156902 | A | 10/2020 |

OTHER PUBLICATIONS

JP-2014132964-A—English Translation (Year: 2014).*

International Search Report issued in International Bureau of WIPO Patent Application No. PCT/JP2022/022610, dated Aug. 9, 2022, along with an English translation thereof.

Notice of Reasons for Refusal issued in Japanese Patent Application No. 2021-109212, dated Sep. 3, 2024, together with an English translation.

Office Action issued in European Patent Application No. 22832709.4, dated Jun. 10, 2025.

First Office Action issued in Chinese Patent Application No. 202280015208.3, dated Dec. 27, 2025, together with an English translation.

Second Office Action issued in Chinese Patent Application No. 202280015208.3, dated Jun. 10, 2026, together with an English translation.

* cited by examiner

ENDOSCOPE

TECHNICAL FIELD

The present invention relates to an endoscope.

The present application claims priority based on Japanese Patent Application No. 2021-109212 filed on Jun. 30, 2021, the entire contents of which are incorporated herein by reference.

BACKGROUND ART

Conventionally, in an endoscope, an observation window for observing a subject is provided at a distal end of an insertion portion to be inserted into a body. Dirt such as mucus, blood, and residue is likely to adhere to a surface of such observation window. When dirt or the like adheres to the observation window in this manner, it is difficult to take a clear image of the subject.

In contrast, Patent Literature 1 discloses an endoscope including two nozzles at a distal end of an insertion portion in which such two nozzles can simultaneously inject fluid (air or water).

Patent Literature 2 discloses an endoscope including an operation unit having a two-stage pressing structure, the endoscope capable of switching between air and water when a fluid is supplied to a nozzle at a distal end of an insertion portion by a user appropriately operating the operation unit.

CITATION LIST

Patent Literature

Patent Literature 1: JP 2014-230673 A
Patent Literature 2: JP 2005-270216 A

SUMMARY OF INVENTION

Technical Problem

However, in the endoscopes of Patent Literatures 1 and 2, fluid channels that send air or water to the nozzle are branched or merged on the way, and there is possibility that an air pressure or a water pressure decreases, and an injection force of air or water injected from the nozzle to an observation window decreases, thereby decreasing cleaning power.

The present invention has been achieved in view of such circumstances, and an object thereof is to provide an endoscope capable of preventing a decrease in injection force of a fluid injected from a nozzle to an observation window.

Solution to Problem

An endoscope according to the present invention is an endoscope including a plurality of nozzles that injects a fluid toward an observation window, and an operation unit that operates the injection of the fluid by the nozzles, in which a plurality of fluid channels that supplies the fluid from the operation unit to the nozzles is provided independently, and each nozzle performs the injection non-simultaneously.

In the present invention, since a plurality of fluid channels that supplies the fluid from the operation unit to each nozzle is independently provided without branching or merging on the way, it is possible to prevent a decrease in injection force of the fluid injected from the nozzle to the observation window.

Advantageous Effects of Invention

According to the present invention, an endoscope capable of preventing a decrease in injection force of a fluid injected from a nozzle to an observation window may be provided.

DESCRIPTION OF EMBODIMENTS

Hereinafter, an endoscope according to embodiments of the present invention will be described in detail with reference to the drawings.

First Embodiment

Figure 1:
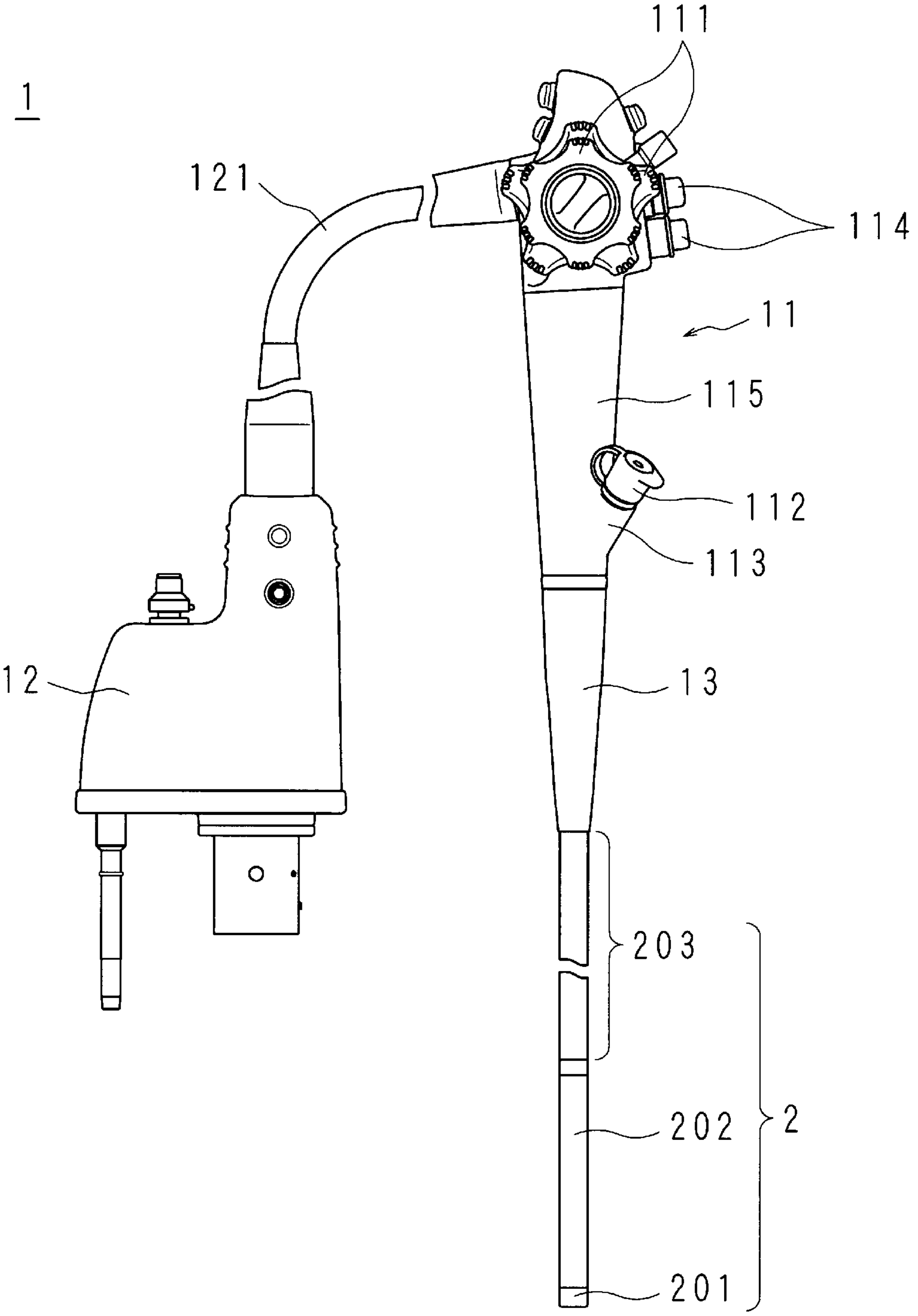
FIG. 1 is an external view of an endoscope according to an embodiment of the present invention.

FIG. 1 is an external view of an endoscope according to an embodiment of the present invention.

An endoscope 1 is a flexible scope for an upper gastrointestinal tract or a lower gastrointestinal tract. The endoscope 1 includes an operation unit 11, a connector unit 12, and an insertion portion 2. A bend preventing portion 13 is provided between the insertion portion 2 and the operation unit 11.

The operation unit 11 includes a substantially cylindrical case 115. One end portion of the case 115 is provided with an operation knob 111 and a button 114 that receive a user's operation, and the other end portion is provided with a channel inlet 113. The channel inlet 113 is provided with a forceps plug 112.

The connector unit 12 is connected to the operation unit 11 via a universal cord 121. The connector unit 12 is connected to a processor for an endoscope, a light source device, a display device, an air supply/water supply device and the like (not illustrated). A fluid channel of a cleaning fluid (air or water), a power line, and a signal line not illustrated from the connector unit 12 to the insertion portion 2 are wired through the universal cord 121, the operation unit 11, the bend preventing portion 13, and the insertion portion 2. When a user appropriately operates the operation unit 11, a fluid sent via the connector unit 12 is sent to the insertion portion 2 via the operation unit 11 and the bend preventing portion 13.

The bend preventing portion 13 communicates with the other end portion of the operation unit 11 and has a cylindrical shape a diameter of which decreases toward the insertion portion 2 side.

The insertion portion 2 has an elongated tubular shape and includes a distal end portion 201, a bending section 202, and a soft portion 203 in this order from a distal end side. The distal end portion 201 is the shortest and rigid. The bending section 202 has flexibility. The soft portion 203 is the longest and flexible.

Figure 2:
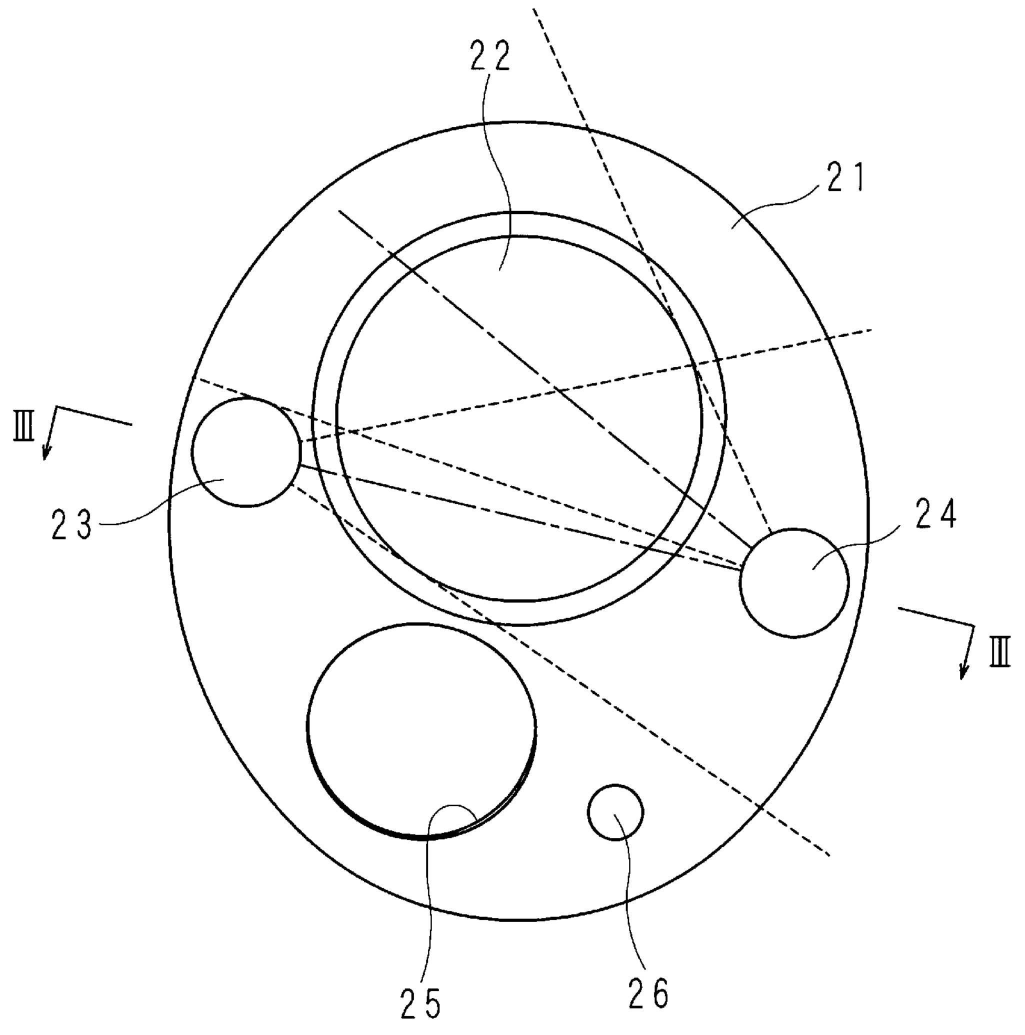
FIG. 2 is a diagram illustrating a distal end surface of a distal end portion of an endoscope according to a first embodiment of the present invention.
Figure 3:
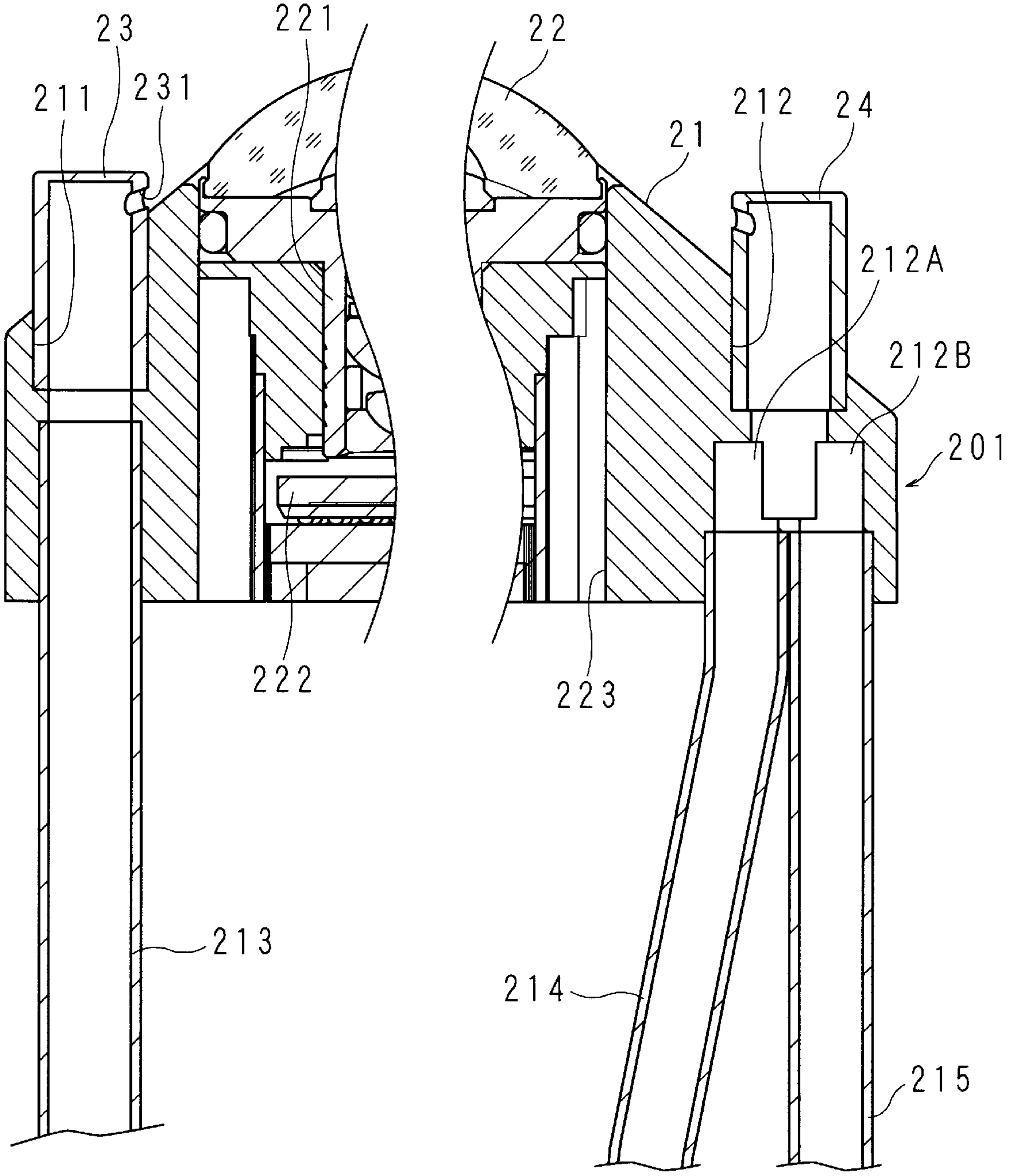
FIG. 3 is a cross-sectional view taken along line III-III in FIG. 2.
Figure 4:
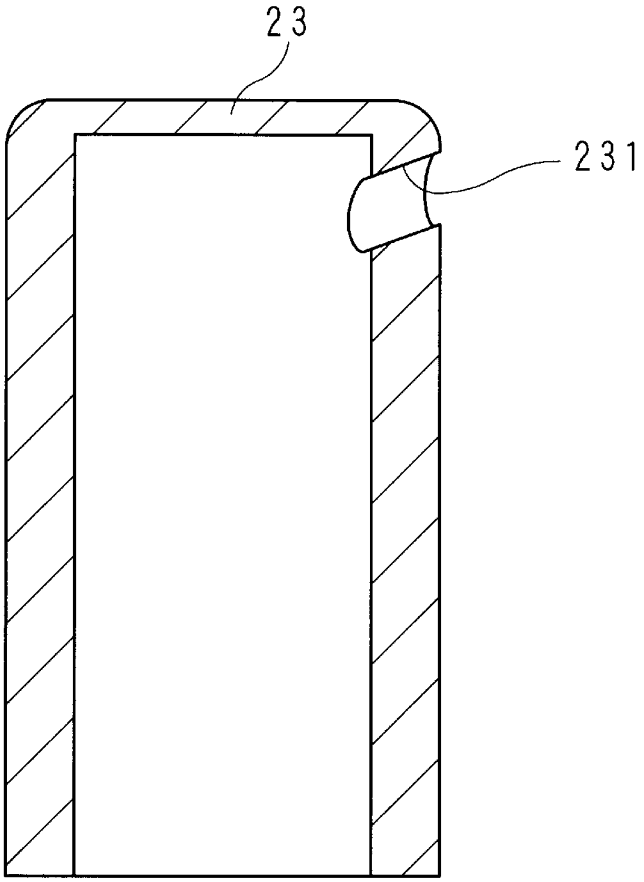
FIG. 4 is a cross-sectional view illustrating an air supply/water supply nozzle of the endoscope according to the first embodiment of the present invention.

FIG. 2 is a diagram illustrating a distal end surface 21 of the distal end portion 201 of the endoscope 1 according to a first embodiment of the present invention, FIG. 3 is a cross-sectional view taken along line III-III in FIG. 2, and FIG. 4 is a cross-sectional view of an air supply/water supply nozzle 23 of the endoscope 1 according to the first embodiment of the present invention.

The distal end portion 201 is substantially elliptical in cross section, and has a distal end protruding in a substantially conical shape (refer to FIG. 3). The distal end surface 21 of the distal end portion 201 is provided with an observation window 22, air supply/water supply nozzles 23 and 24, a channel outlet 25, an illumination 26 and the like. The air supply/water supply nozzles 23 and 24 and the channel outlet 25 are provided adjacently to the observation window 22.

A through hole 223 that penetrates the distal end portion 201 in a longitudinal direction of the insertion portion 2 is formed in a substantially central part of the distal end surface 21 of the distal end portion 201, and the observation window 22 is internally fitted to the through hole 223. The observation window 22 is an objective lens an exposed one surface of which has a convex shape, and a lens unit 221 including a plurality of lenses is arranged on the other surface side of the observation window 22 along an axial center of the distal end portion 201. On a side closer to the bending section 202 than the lens unit 221, an image sensor 222 that captures image light of a subject via the observation window 22 and the lens unit 221 and performs imaging is provided.

The distal end surface 21 of the distal end portion 201 is an inclined surface that is inclined from an edge of the through hole 223 in a tangential direction of the observation window 22, and the air supply/water supply nozzles 23 and 24 and the channel outlet 25 are formed on such inclined surface.

The air supply/water supply nozzles 23 and 24 are provided on both sides across the observation window 22. That is, the air supply/water supply nozzles 23 and 24 are provided on the opposite sides across the observation window 22, but they do not face each other in a radial direction of the observation window 22.

As illustrated in FIG. 4, the air supply/water supply nozzle 23 has a bottomed cylindrical shape. In the air supply/water supply nozzle 23, an injection port 231 is formed on a peripheral wall of an end portion on a bottom side. The injection port 231 has, for example, an oval shape extending in a circumferential direction of the air supply/water supply nozzle 23, and is opened toward the observation window 22. The injection port 231 is also opened obliquely with respect to an axial center of the air supply/water supply nozzle 23. That is, in the injection port 231, an outer edge is formed closer to the bottom than an inner edge. The air supply/water supply nozzle 24 has the same shape as that of the air supply/water supply nozzle 23, and a detailed description thereof will be omitted.

As illustrated in FIG. 3, a through hole 211 circular in cross section that penetrates the distal end portion 201 in an axial direction is formed in the vicinity of the observation window 22 on the distal end surface 21. The through hole 211 has an expanded diameter at both end portions. A part of the air supply/water supply nozzle 23 is internally fitted to one end side on the distal end surface 21 side of the through hole 211, and one end of the fluid channel 213 is internally fitted to the other end side of the through hole 211. The fluid channel 213 extends through the insertion portion 2 to an air supply/water supply valve 3 of the operation unit 11 to be described later.

A through hole 212 circular in cross section that penetrates the distal end portion 201 in the axial direction is formed in the vicinity of the observation window 22 on the distal end surface 21. A diameter of the through hole 212 on one end side on the distal end surface 21 side is expanded. A part of the air supply/water supply nozzle 24 is internally fitted to one end side of the through hole 212. The other end side of the through hole 212 is divided into a first end 212A and a second end 212B. One ends of the fluid channels 214 and 215 are internally fitted to the first end 212A and the second end 212B, respectively. The fluid channels 214 and 215 extend through the insertion portion 2 to the air supply/water supply valve 3 of the operation unit 11.

That is, one end of the fluid channel 213 is connected to the air supply/water supply nozzle 23, and the other end thereof is connected to the air supply/water supply valve 3. One ends of the fluid channels 214 and 215 are connected to the air supply/water supply nozzle 24, and the other ends thereof are connected to the air supply/water supply valve 3. The fluid channels 213, 214, and 215 are provided independently. That is, there is no branching or merging in the fluid channels 213, 214, and 215 between the air supply/water supply nozzles 23 and 24 and the air supply/water supply valve 3.

As described above, the fluid supplied from the air supply/water supply device via the connector unit 12 is sent to the air supply/water supply nozzles 23 and 24 through the fluid channels 213, 214, and 215 via the air supply/water supply valve 3. For example, the fluid channels 213 and 214 are for water supply, and the fluid channel 215 is for air supply. Air and water supplied to the air supply/water supply nozzles 23 and 24 are injected toward the observation window 22.

In FIG. 2, a broken line indicates a fluid injection range in each of the air supply/water supply nozzles 23 and 24, and a dashed-dotted line indicates an injection direction in each of the air supply/water supply nozzles 23 and 24. In other words, the injection direction is a direction of a line that bisects the injection range.

As illustrated in FIG. 2, the injection range (refer to the broken line) of each of the air supply/water supply nozzles 23 and 24 is a partial surface of the observation window 22 including the center of the observation window 22. The injection direction (refer to the dashed-dotted line) of each of the air supply/water supply nozzles 23 and 24 is offset from the center of the observation window 22. That is, the dashed-dotted line that bisects the injection range of each of the air supply/water supply nozzles 23 and 24 is offset from the center of the observation window 22. The injection direction of the air supply/water supply nozzle 23 intersects with the injection direction of the air supply/water supply nozzle 24, a combined injection range of the air supply/water supply nozzles 23 and 24 at least covers an entire surface of the observation window 22, and the sum of the injection ranges of all the air supply/water supply nozzles 23 and 24 is wider than the entire surface of the observation window 22.

The operation unit 11 includes two buttons 114; one for water supply and air supply, and the other for suction operation. Specifically, the operation unit 11 includes the water supply/air supply valve 3 and a suction valve, and the water supply/air supply valve 3 and the suction valve are operated by the buttons 114. The water supply/air supply valve 3 adjusts supply of the fluid to the fluid channels 213, 214, and 215. The suction valve sucks a residue and the like to discharge from the body.

Figure 5:
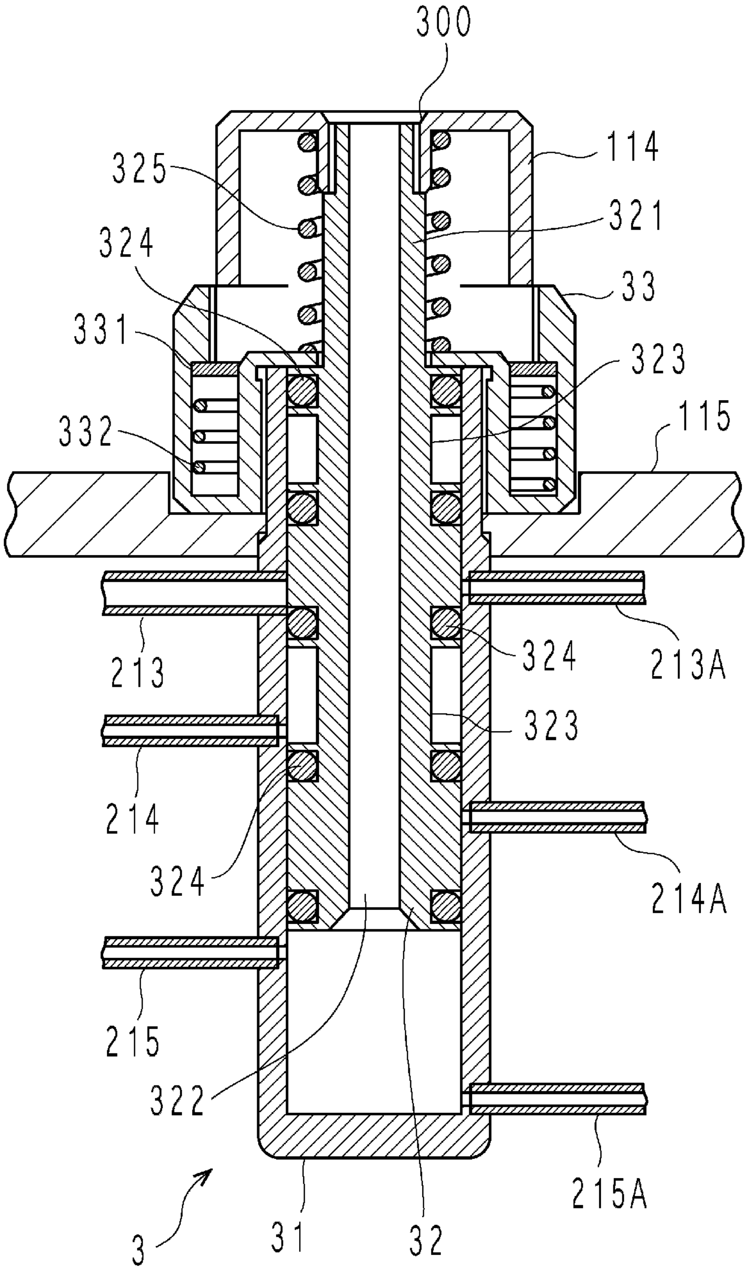
FIG. 5 is a cross-sectional view illustrating a configuration of an air supply/water supply valve included in an operation unit of the endoscope according to the first embodiment of the present invention.

FIG. 5 is a cross-sectional view illustrating a configuration of the air supply/water supply valve 3 included in the operation unit 11 of the endoscope 1 according to the first embodiment of the present invention.

The air supply/water supply valve 3 includes a cylinder 31 and a piston 32. The cylinder 31 has a cylindrical shape with a bottom at one end, and the piston 32 has a substantially round bar shape. The piston 32 is inserted into the cylinder 31, slides on an inner peripheral surface of the cylinder 31 in an axial direction of the cylinder 31, and a retractable unit 321 close to one end of the piston 32 protrudes from and retracts into the cylinder 31.

The cylinder 31 is attached to the case 115, and the other end portion thereof is exposed from the case 115. The other ends of the fluid channels 213, 214, and 215 are connected to the cylinder 31. One ends of upstream channels 213A, 214A, and 215A corresponding to the fluid channels 213, 214, and 215, respectively, are connected to the cylinder 31. The other ends of the upstream channels 213A, 214A, and 215A are connected to the connector unit 12, and send the fluid supplied from the air supply/water supply device via the connector unit 12 to the air supply/water supply valve 3. The upstream channels 213A, 214A, and 215A correspond to the fluid channels 213, 214, and 215, respectively. That is, water is supplied via the upstream channels 213A and 214A, and air is supplied via the upstream channel 215A.

A button receiver 33 is provided so as to cover the one end portion of the cylinder 31. The button receiver 33 has a substantially cylindrical shape, and a bottomed cylindrical button 114 is inserted from one end side of the button receiver 33. The button receiver 33 includes an outer cylindrical wall and an inner cylindrical wall arranged coaxially with the outer cylindrical wall, and the outer cylindrical wall is arranged at a predetermined interval from the inner cylindrical wall. One end portion of the inner cylindrical wall protrudes inward, and the outer cylindrical wall and the inner cylindrical wall are connected only at the other end. The outer cylindrical wall is longer than the inner cylindrical wall in the axial direction of the button receiver 33. An inner diameter of the outer cylindrical wall is slightly larger than an outer diameter of the button 114, and the button 114 is guided by an inner peripheral surface of the outer cylindrical wall to slide in an axial direction. An inner diameter of the inner cylindrical wall is slightly larger than an outer diameter of the cylinder 31, and one end portion of the cylinder 31 is internally fitted to the inner cylindrical wall.

An annular member 331 that abuts the button 114 and a spring 332 that biases the annular member 331 toward the button 114 are inserted between the outer cylindrical wall and the inner cylindrical wall. That is, the annular member 331 and the spring 332 are externally fitted to the inner cylindrical wall.

The piston 32 includes a through hole 322 that penetrates the axial center, and a diameter thereof is reduced at the retractable unit 321. The retractable unit 321 extends through the inside of the inner cylindrical wall in an axial direction of the button receiver 33. A spring 325 is externally fitted to the retractable unit 321. The retractable unit 321 is provided with a step on an outer peripheral surface of one end thereof, and an interval is formed between the same and the spring 325.

A portion other than the retractable unit 321 of the piston 32 (hereinafter, referred to as a portion other than the retractable unit 321) is always inserted in the cylinder 31. In the portion other than the retractable unit 321, five O-rings 324 are provided on the outer peripheral surface. In the portion other than the retractable unit 321, recesses are formed in a circumferential direction at substantially regular intervals in an axial direction of the piston 32, and the O-ring 324 is accommodated in each recess.

In the portion other than the retractable unit 321, cutouts 323 are formed in the circumferential direction between first and second O-rings 324 and between third and fourth O-rings 324 from the retractable unit 321 side.

In the button 114, a through hole 300 that penetrates the bottom of the button 114 is formed at a position corresponding to the through hole 322 of the piston 32, and a fitted cylinder extending inward in the axial direction of the button 114 is circumferentially provided at an edge of the through hole 300. Such fitted cylinder of the button 114 is externally fitted to the outer peripheral surface of the one end of the retractable unit 321. That is, the fitted cylinder of the button 114 is interposed between the retractable unit 321 and the spring 325.

With the above-described configuration, in the endoscope 1 according to the first embodiment of the present invention, the injection of air and water in the air supply/water supply nozzles 23 and 24 can be independently adjusted using the operation unit 11 (button 114). Therefore, in the endoscope 1, it is possible to prevent simultaneous injection of air and water in the air supply/water supply nozzles 23 and 24.

Figure 6:
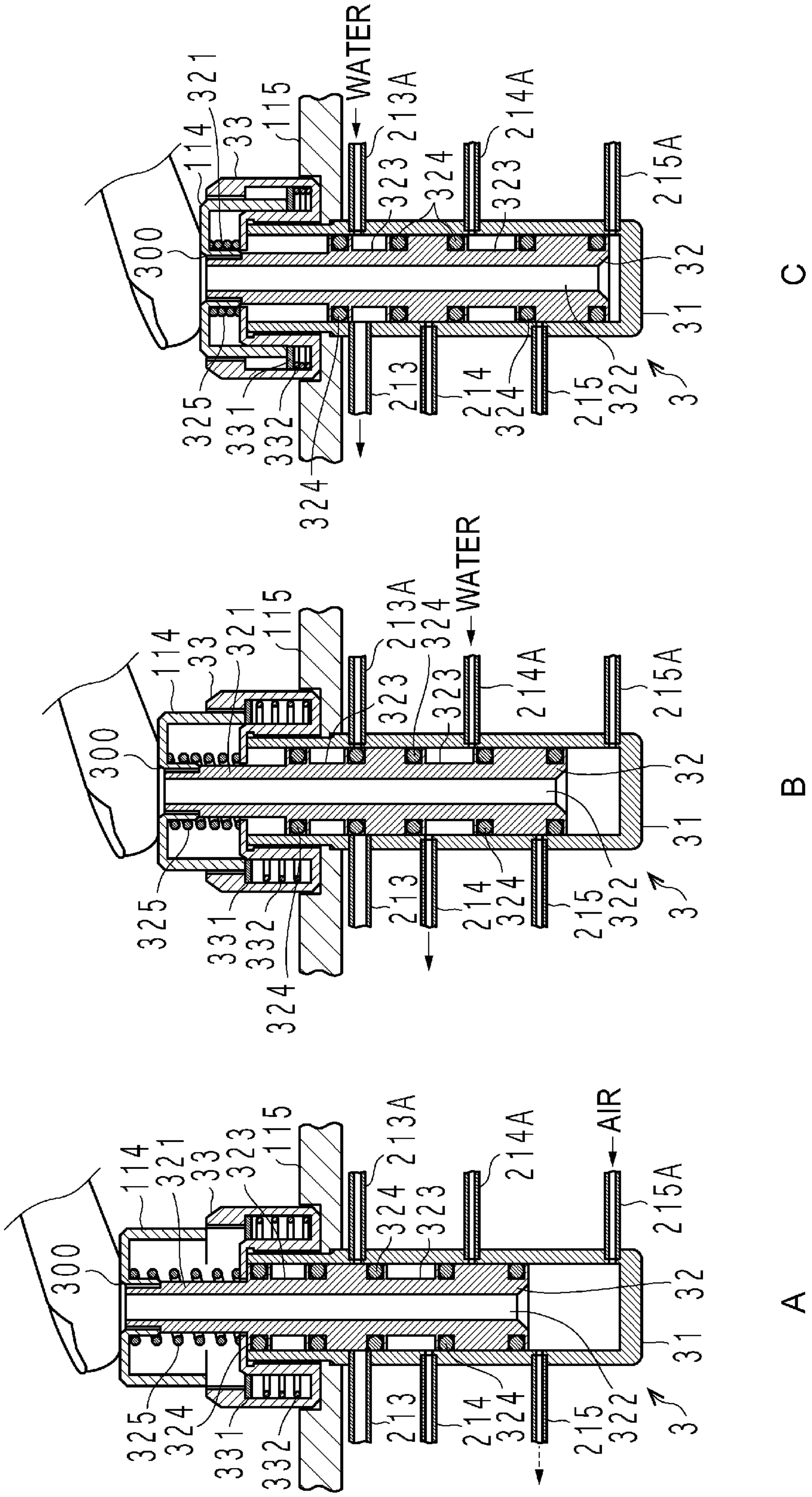
FIG. 6 is a diagram for explaining a method of operating a button for adjusting injection of air and water.

FIG. 6 is a diagram for explaining a method of operating the button 114 for adjusting injection of air and water. FIG. 5 illustrates a state before the operation is started, and a position of the piston 32 illustrated in FIG. 5 is an original position.

As illustrated in FIG. 5, in a case where the piston 32 is at the original position, the upstream channels 213A and 214A are blocked by the piston 32, and only the upstream channel 215A is opened. Therefore, air flowing through the upstream channel 215A flows into the cylinder 31. However, since the through hole 322 is opened outward via the through hole 300 of the button 114 as described above, the air flowing into the cylinder 31 leaks from the through hole 300 of the button 114 outward via the through hole 322.

In contrast, as illustrated in FIG. 6A, in a case where the user places his/her fingertip on the button 114 to block the through hole 300, the air flowing into the cylinder 31 from the upstream channel 215A does not leak, but flows into the fluid channel 215 to be supplied to the air supply/water supply nozzle 24.

Next, as illustrated in FIG. 6B, in a case where the user presses the button 114 until the spring 325 is compressed and the button 114 abuts the annular member 331 of the button receiver 33 (hereinafter, referred to as a first-stage operation), the piston 32 moves, the upstream channel 213A is blocked by the piston 32, and only the upstream channels 214A and 215A are opened in the cylinder 31. However, the piston 32 blocks the fluid channel 215 corresponding to the upstream channel 215A. Therefore, the fluid cannot be supplied via the fluid channels 213 and 215.

In contrast, the upstream channel 214A communicates with the cutout 323 of the piston 32, and such cutout 323 is formed on an entire circumference of the piston 32. Therefore, the upstream channel 214A communicates with the fluid channel 214 via the cutout 323. Water flowing from the upstream channel 214A flows into the fluid channel 214 through the cutout 323 and is supplied to the air supply/water supply nozzle 24.

As illustrated in FIG. 6C, in a case where the user further presses the button 114 in such a manner that the spring 332 is compressed and the annular member 331 moves to the other end side of the button receiver 33 (hereinafter, referred to as a second-stage operation), the piston 32 moves, the upstream channel 215A is opened in the cylinder 31, and the upstream channels 213A and 214A communicate with the cutout 323 of the piston 32. However, the piston 32 blocks the fluid channels 214 and 215 corresponding to the upstream channels 214A and 215A, respectively. Therefore, the fluid cannot be supplied via the fluid channels 214 and 215.

In contrast, the upstream channel 213A communicates with the cutout 323 of the piston 32, and such cutout 323 is formed on the entire circumference of the piston 32. Therefore, the upstream channel 213A communicates with the fluid channel 213 via the cutout 323. Water flowing from the upstream channel 213A flows into the fluid channel 213 through the cutout 323 and is supplied to the air supply/water supply nozzle 23.

In this manner, in the endoscope 1 according to the first embodiment of the present invention, the injection of the fluid from the air supply/water supply nozzles 23 and 24 to the observation window 22 is non-simultaneously and sequentially performed. Therefore, it is possible to prevent reduction in cleaning effect of the observation window 22 when the fluids injected from the air supply/water supply nozzles 23 and 24 collide to cancel each other in advance.

In a case of the first-stage operation in FIG. 6B, water injected from the air supply/water supply nozzle 24 cleans substantially half the surface of the observation window 22 including the central part of the observation window 22 as illustrated in FIG. 2. In a case of the second-stage operation in FIG. 6C, water injected from the air supply/water supply nozzle 23 cleans substantially half the surface including the central part of the observation window 22 in addition to the remaining surface as illustrated in FIG. 2. Therefore, the entire surface of the observation window 22 is cleaned.

Therefore, in the endoscope 1 according to the first embodiment of the present invention, the entire surface of the observation window 22 can be effectively cleaned using the air supply/water supply nozzles 23 and 24 the injection range of which is narrower than the entire surface of the observation window 22. Furthermore, since the air supply/water supply nozzles 23 and 24 having the narrow injection range are used, it is not necessary to increase diameters of the fluid channels 213 and 214 and the upstream channels 213A and 214A, and the endoscope 1 can be made compact.

In the endoscope 1 according to the first embodiment of the present invention, as described above, the fluid channels 213, 214, and 215 are not branched or merged between the air supply/water supply nozzles 23 and 24 and the air supply/water supply valve 3, and are independent from each other. Therefore, it is possible to prevent a decrease in fluid injection force in the air supply/water supply nozzles 23 and 24.

A case where the user manually operates the button 114 is described above as an example, but the present invention is not limited to this. For example, closing of the through hole 300 of the button 114 by the user, the first-stage operation, and the second-step operation may be automatically controlled.

Although a case where the endoscope 1 includes the two air supply/water supply nozzles 23 and 24 is described above as an example, but the present invention is not limited to this. The number of air supply/water supply nozzles may be three or more, and it is sufficient that the sum of the injection ranges of all the air supply/water supply nozzles is wider than the entire surface of the observation window 22.

Although a case where areas of the injection ranges of the air supply/water supply nozzles 23 and 24 are substantially the same is described above as an example, but the present invention is not limited to this. The areas of the injection ranges of the air supply/water supply nozzles 23 and 24 are not necessarily the same, and it is sufficient that the sum of the injection ranges of all the air supply/water supply nozzles is wider than the entire surface of the observation window 22.

Second Embodiment

Figure 7:
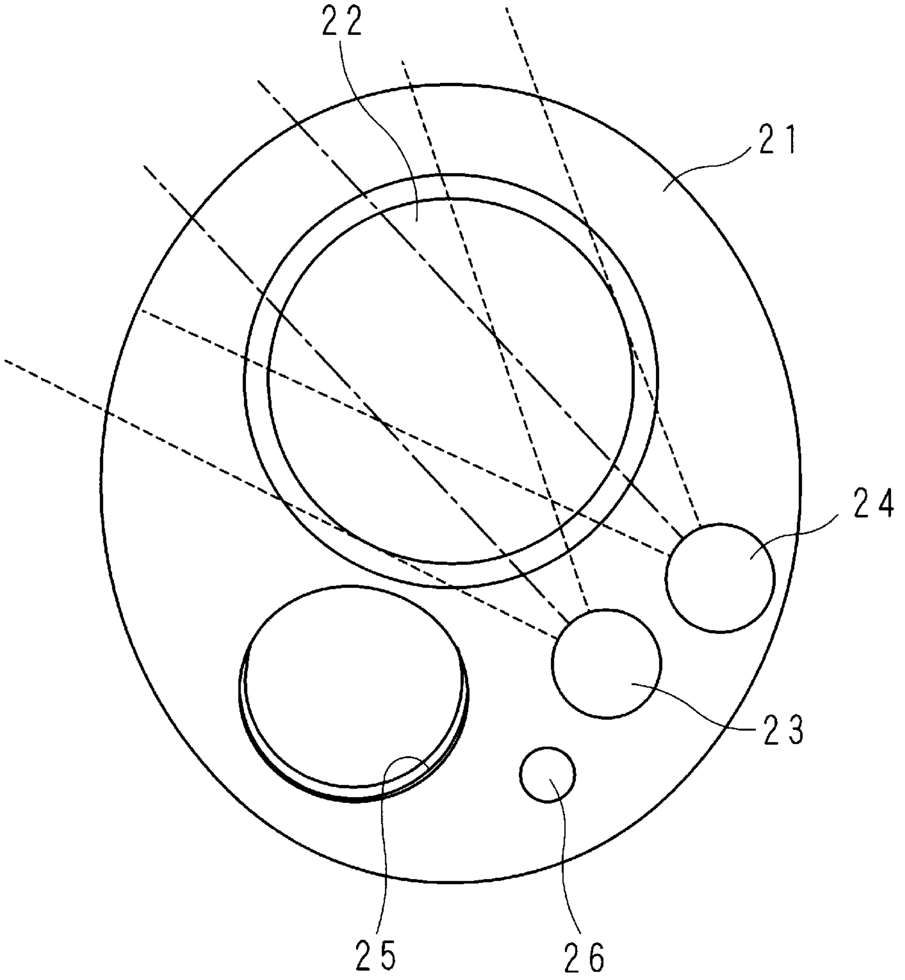
FIG. 7 is a diagram illustrating a distal end surface of a distal end portion of an endoscope according to a second embodiment of the present invention.

FIG. 7 is a diagram illustrating a distal end surface 21 of a distal end portion 201 of an endoscope 1 according to a second embodiment of the present invention. In FIG. 7, a broken line indicates a fluid injection range in each of air supply/water supply nozzles 23 and 24, and a dashed-dotted line indicates an injection direction in each of the air supply/water supply nozzles 23 and 24.

The distal end surface 21 of the distal end portion 201 is provided with an observation window 22, air supply/water supply nozzles 23 and 24, a channel outlet 25, an illumination 26 and the like. The air supply/water supply nozzles 23 and 24 and the channel outlet 25 are provided adjacently to the observation window 22. The air supply/water supply nozzles 23 and 24 are adjacent to each other.

In the second embodiment also, as in the first embodiment, the injection range (refer to the broken line) of each of the air supply/water supply nozzles 23 and 24 is a partial surface of the observation window 22 including the center of the observation window 22. The injection direction (refer to the dashed-dotted line) of each of the air supply/water supply nozzles 23 and 24 is offset from the center of the observation window 22. That is, that is, the dashed-dotted line that bisects the injection range of each of the air supply/water supply nozzles 23 and 24 is offset from the center of the observation window 22. The injection direction of the air supply/water supply nozzle 23 is parallel to the injection direction of the air supply/water supply nozzle 24, and the sum of the injection ranges of all the air supply/water supply nozzles 23 and 24 at least covers an entire surface of the observation window 22.

In the endoscope 1 according to the second embodiment of the present invention also, as in the first embodiment, when a user performs a first-stage operation and a second-stage operation of a button 114, the fluid is non-simultaneously and sequentially injected from the air supply/water supply nozzles 23 and 24 to the observation window 22. Therefore, it is possible to prevent reduction in cleaning effect of the observation window 22 when the fluids injected from the air supply/water supply nozzles 23 and 24 collide to cancel each other in advance.

Water injected from the air supply/water supply nozzle 24 in a case of the first-stage operation cleans substantially half the surface of the observation window 22 including the center part of the observation window 22, and water injected from the air supply/water supply nozzle 23 in a case of the second-stage operation cleans substantially half the surface including the central part of the observation window 22 in addition to the remaining surface. Therefore, the entire surface of the observation window 22 can be effectively cleaned using the air supply/water supply nozzles 23 and 24 the injection range of which is narrower than the entire surface of the observation window 22. Since the air supply/water supply nozzles 23 and 24 having narrow injection ranges are used, it is not necessary to increase diameters of fluid channels 213 and 214 and upstream channels 213A and 214A, and the endoscope 1 can be made compact.

Parts similar to those in the first embodiment are denoted by the same reference numerals, and detailed descriptions thereof are omitted.

Third Embodiment

Figure 8:
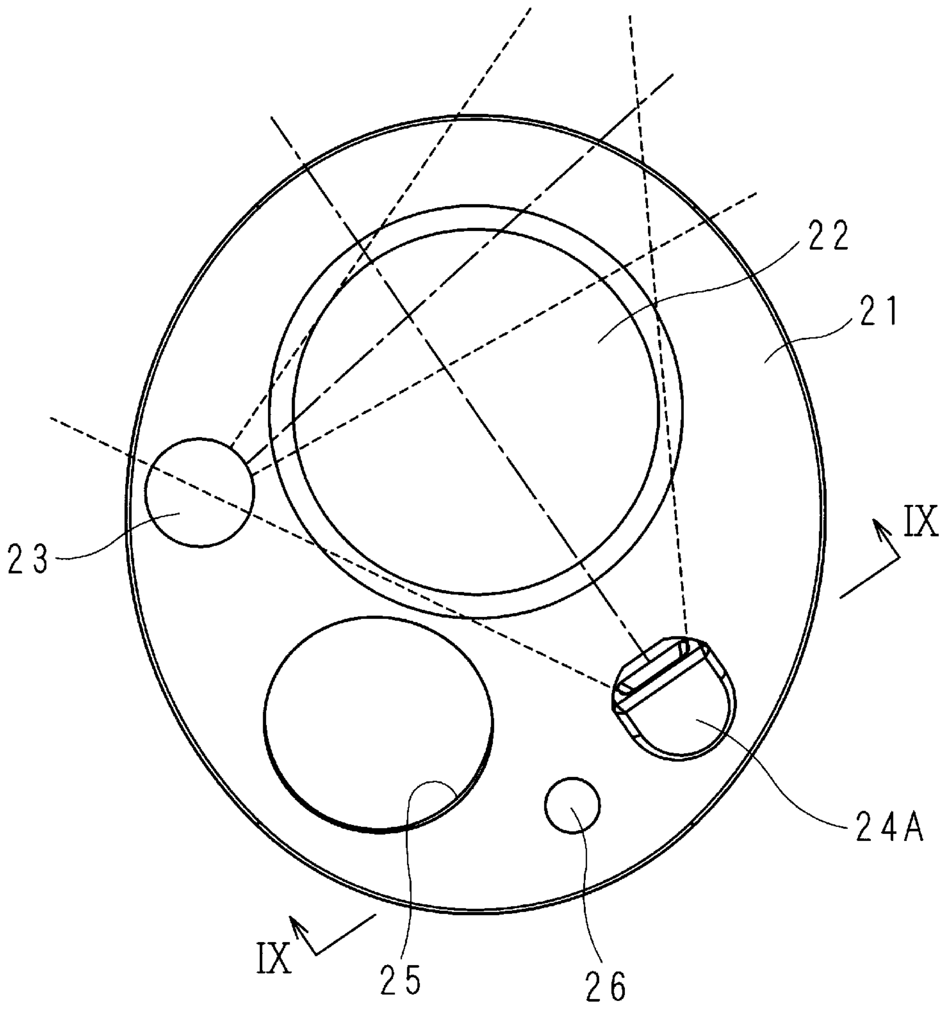
FIG. 8 is a diagram illustrating a distal end surface of a distal end portion of an endoscope according to a third embodiment of the present invention.
Figure 9:
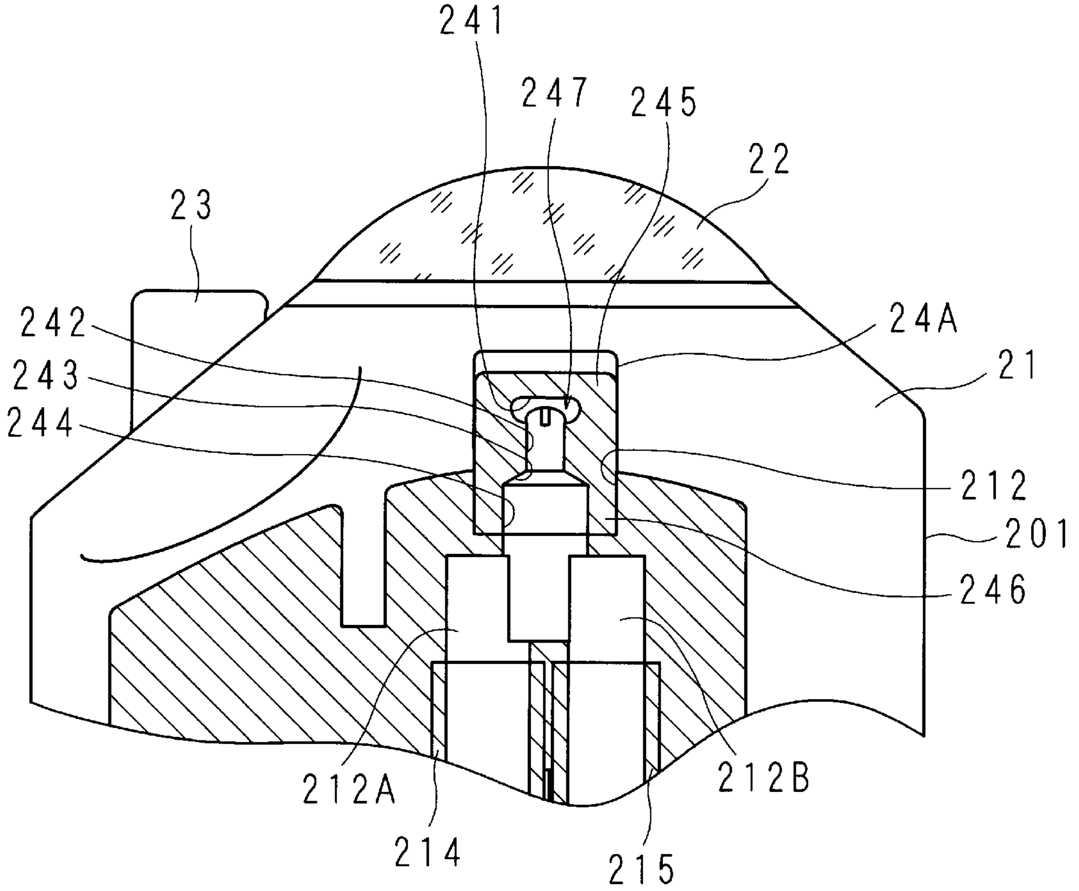
FIG. 9 is a cross-sectional view taken along line IX-IX in FIG. 8.
Figure 10:
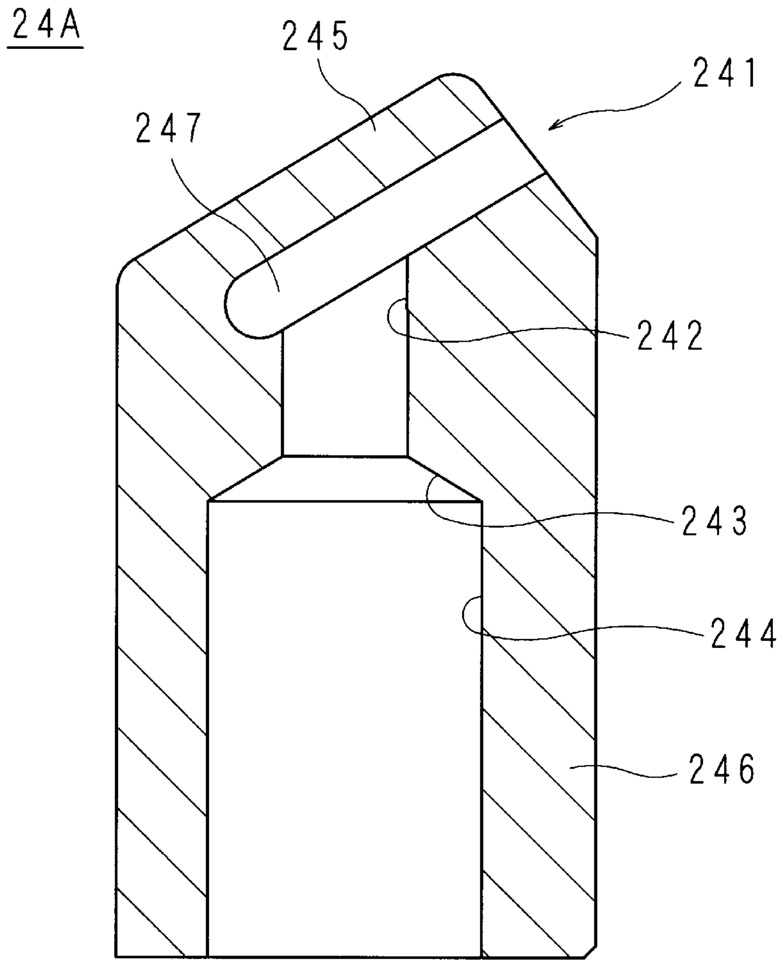
FIG. 10 is a cross-sectional view illustrating an air supply/water supply nozzle of the endoscope according to the third embodiment of the present invention.

FIG. 8 is a diagram illustrating a distal end surface 21 of a distal end portion 201 of an endoscope 1 according to a third embodiment of the present invention, FIG. 9 is a cross-sectional view taken along line IX-IX in FIG. 8 and FIG. 10 is a cross-sectional view of an air supply/water supply nozzle 24A of the endoscope 1 according to the third embodiment of the present invention. In FIG. 8, a broken line indicates a fluid injection range in each of air supply/water supply nozzles 23 and 24A, and a dashed-dotted line indicates an injection direction in each of the air supply/water supply nozzles 23 and 24A.

The distal end surface 21 of the distal end portion 201 is provided with an observation window 22, an air supply/water supply nozzle 23 (second nozzle), an air supply/water supply nozzle 24A (first nozzle), a channel outlet 25, an illumination 26 and the like. The air supply/water supply nozzles 23, the air supply/water supply nozzle 24A, and the channel outlet 25 are provided adjacently to the observation window 22.

The air supply/water supply nozzle 23 and the air supply/water supply nozzle 24A are provided on both sides across the observation window 22. That is, the air supply/water supply nozzle 23 and the air supply/water supply nozzle 24A are provided on the opposite sides across the observation window 22, but they do not face each other in a radial direction of the observation window 22. As illustrated in FIG. 8, the injection range of the air supply/water supply nozzle 24A is wider than the injection range of the air supply/water supply nozzle 23. The injection direction of the air supply/water supply nozzle 23 intersects with the injection direction of the air supply/water supply nozzle 24A.

The air supply/water supply nozzle 24A includes an outlet 241 from which air or water is emitted. Air and water are emitted toward the observation window 22 via the outlet 241. The outlet 241 has a substantially oval shape. A part of the air supply/water supply nozzle 24A is internally fitted to a through hole 212.

The air supply/water supply nozzle 24A includes a cylindrical portion 246 and a lid portion 245 that seals one open end of the cylindrical portion 246. The lid portion 245 and the cylindrical portion 246 are integrally formed. The outlet 241 is provided on the lid portion 245 side in the air supply/water supply nozzle 24A.

A connection portion 244 and a small diameter portion 242 are provided inside the cylindrical portion 246, and a diameter-reduced portion 243 is formed between the connection portion 244 and the small diameter portion 242. That is, the small diameter portion 242 is provided on a downstream side of the connection portion 244 and has a smaller diameter than that of the connection portion 244. The connection portion 244, the diameter-reduced portion 243, and the small diameter portion 242 are coaxially provided.

The connection portion 244 extends in an axial length direction of the cylindrical portion 246, and air and water sent through fluid channels 214 and 215 flow into the connection portion 244 and are sent to the outlet 241 via the small diameter portion 242.

As described above, the diameter-reduced portion 243 is formed on the downstream side of the connection portion 244 and on an upstream side of the small diameter portion 242. The diameter-reduced portion 243 connects the connection portion 244 and the small diameter portion 242, and has a tapered shape or a funnel shape. That is, in the diameter-reduced portion 243, the diameter is gradually reduced from the connection portion 244 toward the small diameter portion 242. Therefore, a pressure of air or water flowing into the small diameter portion 242 through the diameter-reduced portion 243 increases and a flow speed increases.

The lid portion 245 has a disk shape having a predetermined thickness, and is provided in such a manner that a thickness direction thereof is oblique to a parallel arrangement direction of the connection portion 244, the diameter-reduced portion 243, and the small diameter portion 242. A guide path 247 is formed inside the lid portion 245. The guide path 247 is a cavity cut out into a flat rectangular shape, and guides air or water flowing from the small diameter portion 242 to the outlet 241.

Having such a configuration, the air supply/water supply nozzle 24A can inject high-speed air or water toward the observation window 22 in a wide range.

Note that, the air supply/water supply nozzle 23 has already been described, and a detailed description thereof will be omitted.

The air supply/water supply nozzle 24A injects water toward a surface (hereinafter, referred to as a partial surface) on the air supply/water supply nozzle 24A side out of the surface of the observation window 22. The injection direction (refer to the dashed-dotted line) of the air supply/water supply nozzle 24A passes through the center of the observation window 22, and the injection range (refer to the broken line) of the air supply/water supply nozzle 24A covers the entire surface of the observation window 22 including the center of the observation window 22.

In contrast, the air supply/water supply nozzle 23 injects water toward a surface opposite to the partial surface out of the surface of the observation window 22. The injection range (refer to the broken line) of the air supply/water supply nozzle 23 is a partial surface of the observation window 22 not including the center of the observation window 22, and the injection direction (refer to the dashed-dotted line) of the air supply/water supply nozzle 23 is offset from the center of the observation window 22. Especially, the air supply/water supply nozzle 23 injects the water toward a portion including an edge of the observation window 22.

In the endoscope 1 according to the third embodiment of the present invention also, as in the first embodiment, when a user performs a first-stage operation and a second-stage operation of a button 114, the fluid is non-simultaneously and sequentially injected from the air supply/water supply nozzles 23 and 24A to the observation window 22. Therefore, it is possible to prevent reduction in cleaning effect of the observation window 22 when the fluids injected from the air supply/water supply nozzles 23 and 24A collide to cancel each other in advance.

In a case of the first-stage operation, water is injected from the air supply/water supply nozzle 24A toward the partial surface of the observation window 22. In general, a fluid flowing near a wall surface is attracted to the wall surface by the effect of fluid viscosity (referred to as the Coanda effect). Due to such Coanda effect, the water injected from the air supply/water supply nozzle 24A starts flowing along the partial surface of the observation window 22 and flows to the opposite side of the partial surface to clean the surface of the observation window 22.

The water injected from the air supply/water supply nozzle 23 in a case of the second-stage operation flows through a portion on the side opposite to the partial surface of the observation window 22, the portion including the edge of the observation window 22, and cleans the surface of the observation window 22.

Therefore, the entire surface of the observation window 22 can be effectively cleaned using the air supply/water supply nozzles 23 and 24A. Especially, the air supply/water supply nozzle 23 cleans the edge of the observation window 22 on the side opposite to the partial surface where water might not reach when the observation window 22 is cleaned by the injection of water from the air supply/water supply nozzle 24A, so that the observation window 22 can be cleaned entirely and evenly.

In the endoscope 1 according to the third embodiment of the present invention also, the fluid channels 213, 214, and 215 are independent from each other between the air supply/water supply nozzles 23 and 24A and an air supply/water supply valve 3. Therefore, it is possible to prevent a decrease in fluid injection force in the air supply/water supply nozzles 23 and 24A.

The endoscope 1 according to the embodiments is not limited to the description above. The diameter of the fluid channels 214 and 215 of the air supply/water supply nozzle 24A having a wider injection range than that of the air supply/water supply nozzle 23 may be made larger than that of the fluid channel 213 of the air supply/water supply nozzle 23.

Parts similar to those in the first embodiment are denoted by the same reference numerals, and detailed descriptions thereof are omitted.

REFERENCE SIGNS LIST

1 Endoscope
11 Operation unit
22 Observation window
23 Air supply/water supply nozzle (second nozzle)
24 Air supply/water supply nozzle
24A Air supply/water supply nozzle (first nosale)
213, 214, 215 Fluid channel

The invention claimed is:

1. An endoscope comprising:
an observation window at a distalmost tip of the endoscope;
an annular conical surface extending proximally from and entirely surrounding the observation window;
a plurality of nozzles located on the annular conical surface and that injects a fluid over the observation window;
an instrument channel outlet located on the annular conical surface; and
an operation handle that operates the injection of the fluid by the plurality of nozzles, wherein
a plurality of fluid channels that supplies the fluid from the operation handle to the plurality of nozzles is provided independently,
each nozzle of the plurality of nozzles performs the injection non-simultaneously,
each nozzle of the plurality of nozzles is positioned at an opposite side of the observation window in a radial direction of the observation window,
the plurality of nozzles do not face each other in the radial direction of the observation window, and
the observation window distally extends in a longitudinal direction beyond the plurality of nozzles.

2. The endoscope according to claim 1, wherein
an injection range of each nozzle of the plurality of nozzles is a partial surface of the observation window including a center of the observation window, and
a sum of injection ranges of an entirety of the plurality of nozzles is wider than an entire surface of the observation window.

3. The endoscope according to claim 1, wherein
an injection direction of each nozzle of the plurality of nozzles is offset from a center of the observation window, and
injection directions of the plurality of nozzles are parallel to each other.

4. The endoscope according to claim 1, wherein
an injection direction of each nozzle of the plurality of nozzles is offset from a center of the observation window, and
injection directions of the plurality of nozzles intersect with each other.

5. The endoscope according to claim 1, wherein
the observation window has a convex shape,
the plurality of nozzles includes a first nozzle having a first injection direction of which is directed toward a center of the observation window and a second nozzle having a second injection direction of which is offset from the center of the observation window,
the first nozzle injects toward a surface of the observation window on a side of the first nozzle, and
the second nozzle injects toward a surface on a side opposite to the surface.

6. The endoscope according to claim 5, wherein an injection range of the first nozzle of the plurality of nozzles is wider than an injection range of the second nozzle of the plurality of nozzles.

7. The endoscope according to claim 5, wherein a diameter of a fluid channel of the first nozzle of the plurality of nozzles is larger than a diameter of a fluid channel of the second nozzle of the plurality of nozzles.

8. The endoscope according to claim 1, wherein the plurality of fluid channels includes:
first and second fluid channels that supplies water and air, respectively, to one nozzle of the plurality of nozzles; and
a third fluid channel that supplies water to another nozzle of the plurality of nozzles, and
the first to third fluid channels do not communicate with one another and directly connect the operation handle to the plurality of nozzles.

9. The endoscope according to claim 1, further comprising a distalmost endoscope end having an elliptical cross section.

10. The endoscope according to claim 1, wherein
each nozzle of the plurality of nozzles has an outwardly-angled injection port such that the plurality of nozzles each injects fluid in a distal injection direction.

11. The endoscope according to claim 1, wherein a curve extending from an outer edge of the annular conical surface to a center of the observation window is an uninterrupted, continuous curve.

* * * * *